(12) United States Patent
Tsai et al.

(10) Patent No.: US 12,207,962 B2
(45) Date of Patent: Jan. 28, 2025

(54) METHOD FOR MEASURING MUSCLE MASS

(71) Applicant: National Cheng Kung University, Tainan (TW)

(72) Inventors: Yi-Shan Tsai, Tainan (TW); Yu-Hsuan Lai, Tainan (TW); Bow Wang, Tainan (TW); Cheng-Shih Lai, Tainan (TW); Chao-Yun Chen, Tainan (TW); Meng-Jhen Wu, Tainan (TW); Po-Tsun Kuo, Tainan (TW); Tsung-Han Lee, Tainan (TW)

(73) Assignee: National Cheng Kung University, Tainan (TW)

( * ) Notice: Subject to any disclaimer, the term of this patent is extended or adjusted under 35 U.S.C. 154(b) by 375 days.

(21) Appl. No.: 17/724,516

(22) Filed: Apr. 20, 2022

(65) Prior Publication Data

US 2023/0337998 A1  Oct. 26, 2023

(51) Int. Cl.
*A61B 6/00* (2024.01)
*A61B 6/03* (2006.01)
*A61B 6/50* (2024.01)
*G06T 7/00* (2017.01)

(52) U.S. Cl.
CPC ............ *A61B 6/5217* (2013.01); *A61B 6/032* (2013.01); *A61B 6/50* (2013.01); *G06T 7/0014* (2013.01); *G06T 2207/10081* (2013.01); *G06T 2207/30012* (2013.01)

(58) Field of Classification Search
CPC ......... G06T 7/0012; G06T 2207/10072; G06T 2207/10132; G06T 2207/30004; G06T 2207/30052; G06T 2210/41; G06T 15/04; G06T 17/20; G06T 19/20; G06T 2210/44; G06T 2219/2021; G06T 7/30; G06T 7/50; G06T 7/0014; G06T 2207/10081; G06T 2207/30012; A61F 2/02; A61F 2240/002; A61F 2/0059; A61F 2/14; A61F 2210/009; A61F 2240/001; G02C 7/04; A61B 6/5217; A61B 6/032; A61B 6/50
USPC ................................................... 382/131, 128
See application file for complete search history.

(56) References Cited

U.S. PATENT DOCUMENTS

| | | | | |
|---|---|---|---|---|
| 5,628,328 | A * | 5/1997 | Nissen | G01N 33/48714 600/587 |
| 7,103,134 | B2 * | 9/2006 | Suzuki | A61B 6/032 378/4 |
| 8,792,698 | B2 * | 7/2014 | Goto | G06T 7/0012 382/131 |
| 9,865,050 | B2 * | 1/2018 | Kelly | G06T 7/0012 |
| 11,322,259 | B2 * | 5/2022 | Do | G16H 15/00 |
| 11,915,827 | B2 * | 2/2024 | Neumann | G06N 7/01 |

(Continued)

*Primary Examiner* — Negussie Worku
(74) *Attorney, Agent, or Firm* — Locke Lord LLP; Tim Tingkang Xia, Esq.

(57) ABSTRACT

The present invention relates to a method for measuring muscle mass, including: a first selection step, wherein a frame selection information is obtained by using a frame to select a fascia region from a provided computed tomography image under the condition that the window width ranges from 300 HU to 500 HU and the window level ranges from 40 HU to 50 HU, wherein the selected range of the fascia region includes a muscle; and a second selection step, wherein a muscle information of the muscle is obtained by calculating a pixel value in the frame-selected fascia region under the condition that the HU value of the CT image ranges from −29 HU to 150 HU.

10 Claims, 9 Drawing Sheets

(56) References Cited

U.S. PATENT DOCUMENTS

| | | | | |
|---|---|---|---|---|
| 2004/0066881 A1* | 4/2004 | Reddy | .................... | A61B 6/507 |
| | | | | 600/425 |
| 2006/0204063 A1* | 9/2006 | Nakashima | ............... | G06T 7/11 |
| | | | | 382/128 |
| 2011/0002522 A1* | 1/2011 | Goto | .................... | G06T 7/0012 |
| | | | | 382/131 |
| 2014/0097817 A1* | 4/2014 | Liu | ....................... | H02M 3/157 |
| | | | | 323/283 |
| 2015/0036910 A1* | 2/2015 | Kelly | .................... | G06T 7/0012 |
| | | | | 382/131 |
| 2016/0058408 A1* | 3/2016 | Kim | ........................ | G06T 7/187 |
| | | | | 382/131 |
| 2016/0256127 A1* | 9/2016 | Lee | ........................ | A61B 6/5264 |
| 2017/0209112 A1* | 7/2017 | Yi | ........................ | A61B 6/032 |
| 2017/0294016 A1* | 10/2017 | Lee | ........................ | G06T 11/005 |
| 2018/0199997 A1* | 7/2018 | Pinto De Oliveira | .... | G06T 7/11 |
| 2020/0167921 A1* | 5/2020 | Kelly | .................... | G06T 11/008 |
| 2020/0211710 A1* | 7/2020 | Do | ........................ | G16H 50/30 |
| 2022/0406430 A1* | 12/2022 | Haase | .................... | G06N 3/09 |
| 2022/0406462 A1* | 12/2022 | Haase | .................... | G16H 20/60 |

* cited by examiner

METHOD FOR MEASURING MUSCLE MASS

FIELD OF THE INVENTION

The present invention relates to a measurement method, and more particularly to a method that uses the computed tomography (CT) scan to measure the muscle mass.

BACKGROUND OF THE INVENTION

The sarcopenia is one of the muscle diseases. It will lead to both the reduction of the weight and the degradation of function of the skeletal muscle among the whole body. Some situations are inevitable along with those and will significantly impact the life qualify even will lead to disability, such as slow fragging motion, weaken grip strength, difficulty moving, repeatedly falls, and body weight loss, difficulty moving, repeated falls and body weight loss. Because the sarcopenia usually occurs with older age and chronic disease, the loss outweights the gain if it is not detected early and then appropriately treated in the early stage. The mild symptoms essentially weaken the hands and feet and then increase the probability of falls, and the severe symptoms may lead to disability and long-term bed rest.

The Taiwan patent publication I646943 provides a method for screening the sarcopenia through functional fitness. It asks the test person to stand up from a carrier and then walk around an object along a preset distance, and then determines whether the test person suffers the sarcopenia according to the time required to walk the preset distance around the object. However, the physical ability and exercise ability of the human body unavoidably have certain errors during every measurement, also the physical ability is gradually decreased in accomplish with the accumulation of fatigues and the measurement numbers. Because the measurement results of physical fitness are affected by many external factors, by only referring to the physical ability is difficult to judge the actual status of the sarcopenia and may lead to misjudgment. Besides, the Taiwan patent publication I652039 provides a method and system for simply measuring the sarcopenia. It determines whether a test person is a sarcopenia patient by measuring both walking speed and grip strength of the test person. Understandably, the measuring method is similar with that provided by I646943, and then both have the problems that the result and precision are affected by errors or external factors.

In view of these above problems and disadvantages of the prior arts, it is currently required to provide a method of accurately measuring the muscle mass such that the sarcopenia patients may not miss the golden period of treatment.

SUMMARY OF THE INVENTION

The problem to be solved by the present invention is to measure the muscle mass of human body by automatically framing a fascia area on the computed tomography image and then adjusting out a suitable HU value to heightlight the muscle mass is the framed area.

To achieve the above object, the invention provides a method for measuring muscle mass which comprises two selection steps. In the first selection step a frame selection information is obtained by using a frame to select a fascia region from a provided computed tomography image under the condition that the window width ranges from 300 HU to 500 HU and the window level ranges from 40 HU to 50 HU, wherein the selected range of the fascia region includes a muscle. In the second selection step, a muscle information of the muscle is obtained by calculating a pixel value in the frame-selected fascia region under the condition that the HU value of the CT image ranges from −29 HU to 150 HU.

The invention also provides a method for measuring muscle mass which comprises two selection steps. In the first selection step, a first frame selection information and a second frame selection information are obtained by using a frame to select a first fascia region and a second fascia region from a provided computed tomography image under the condition that the window width ranges from 300 HU to 500 HU and the window level ranges from 40 HU to 50 HU, wherein the first selected range of the fascia region includes a first muscle and the second selected range of the fascia region includes a second muscle. In the second selection step, a first muscle information of the first muscle is obtained by calculating a pixel value in the frame-selected first fascia region and a second muscle information of the first muscle is obtained by calculating a pixel value in the frame-selected second fascia region under the condition that the HU value of the CT image ranges from −29 HU to 150 HU.

Optionally, the computed tomography image is selected from a group consisting of a horizontal computed tomography scan of the third vertebra or a horizontal computed tomography scan of fourth vertebra, and the muscle is chosen from a group consisting of the following: transverse abdominis, rectus abdominis, internal oblique, external oblique, psoas, quadratus lumborum, paraspinal muscle and combinations thereof.

Optionally, the computed tomography image is selected from a group consisting of a horizontal computed tomography scan of the third vertebra or a horizontal computed tomography scan of fourth vertebra, the first muscle is chosen from a group consisting of the following: transverse abdominis, rectus abdominis, internal oblique, external oblique, psoas, quadratus lumborum, paraspinal muscle and combinations thereof, and the second muscle is chosen from a group consisting of the following: transverse abdominis, rectus abdominis, internal oblique, external oblique, psoas, quadratus lumborum, paraspinal muscle and combinations thereof.

Optionally, the present method further comprises a record step to store the frame selection information in a record module after the first selection step and to store the muscle information in the record module after the second selection step.

Optionally, the present method further comprises a record step to store the frame selection information in a record module after the first selection step and to store the first muscle information and the second muscle information in the record module after the second selection step.

Optionally, the present method further comprises using an analysis module to automatically select the fascia region from the computed tomography image in the first selection step, wherein the analysis module receives a frame selection reference object and then organize and summarize a detail feature within the frame selection range of the frame selection reference object, wherein the analysis module use the detail feature to obtain the frame selection information by framing out a portion of the computed tomography image which having the same detail feature.

Optionally, the present method further comprises an intelligent calculation step after the record step, wherein a calculation module is used to present the muscle information in the digital format so as to express one of the following of the muscle: mass, density and distribution, wherein the calculation module communicates with the record module to receive the muscle information through signal.

Optionally, the present method further comprising using an analysis module to automatically select the first fascia region and the second fascia region from the computed tomography image in the first selection step, wherein the analysis module receives a frame selection reference object and then organize and summarize a detail feature within the frame selection range of the frame selection reference object, wherein the analysis module use the detail feature to obtain the first frame selection information and the second frame selection information by framing out a portion of the computed tomography image which having the same detail feature.

Optionally, the present method further comprising an intelligent calculation step after the record step, wherein a calculation module is used to present the first muscle information and the second muscle information in the digital format so as to express one of the following the first muscle and the second muscle: mass, density and distribution, wherein the calculation module communicates with the record module to receive the first muscle information and the second muscle information through signal.

To compare with the prior arts, the effects of the present invention are that the sarcopenia is not determined by measuring the physical ability and that the computed tomography technology is used to obtain accurate muscle mass data. Hence, the accurate determination is available, also the variation of the muscle mass may be traced during the following treatment stage or rehabilitation stage. In addition, the present invention automatically frames out a fascia area to be measured when using the computed tomography to measure the muscle mass. This is very different from the traditional skills that the medical staff manually frame out. Therefore, it can ensure that all the fascia parts of the muscle surface are framed out without any omission for each fame selection. After that, by adjusting the HU value, the muscle parts can be highlighted on the computed tomography image to obtain accurate muscle mass data.

BRIEF DESCRIPTION OF THE DRAWINGS

Other advantages, objectives and features of the present invention will become apparent from the following description referring to the attached drawings.

DETAILED DESCRIPTION OF THE INVENTION

The following is used to describe the first embodiment of the present invention.

Figure 1:
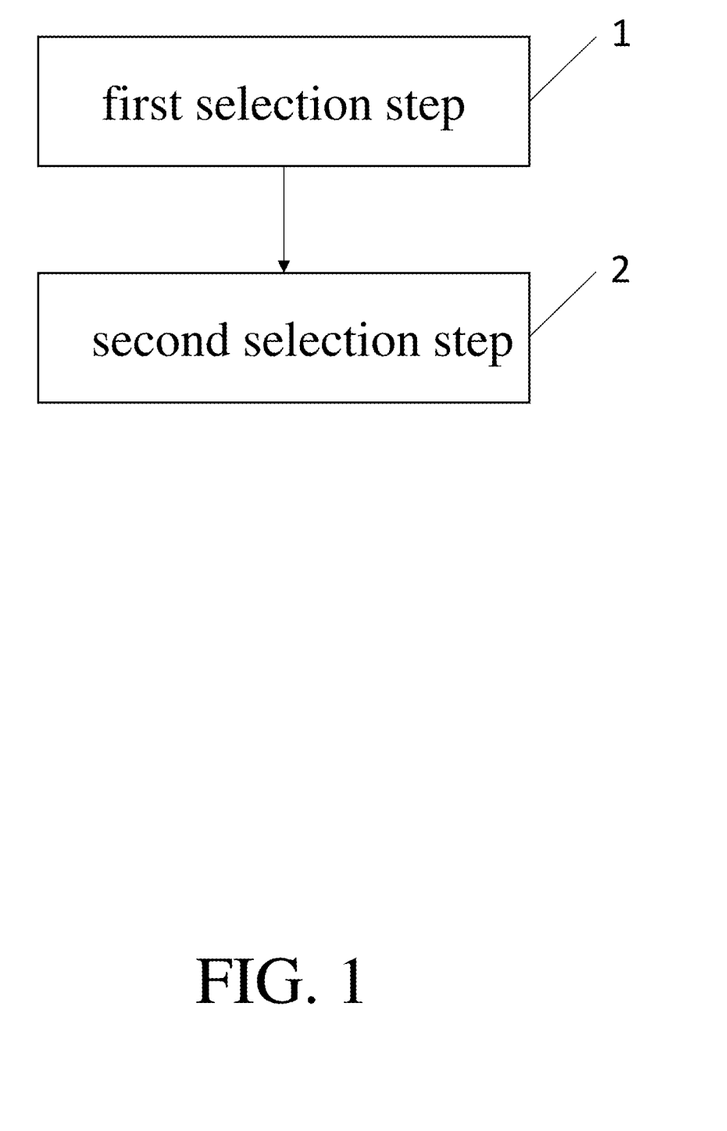
FIG. 1 to FIG. 4 are a series of block diagrams which are used to the discloses the procedure of the method of the invention.

As shown in FIG. 1, the present invention provides a method for measuring muscle mass which comprises two selection steps. In the first selection step a frame selection information is obtained by using a frame to select a fascia region from a provided computed tomography image under the condition that the window width ranges from 300 HU to 500 HU and the window level ranges from 40 HU to 50 HU, wherein the selected range of the fascia region includes a muscle. In the second selection step, a muscle information of the muscle is obtained by calculating a pixel value in the frame-selected fascia region under the condition that the HU value of the CT image ranges from −29 HU to 150 HU. In one preferred embodiment, to measure the muscle mass of the lumbar paraspinal muscles for determining the symptoms or the severity of the sarcopenia, the computed tomography image is optionally selected from but not limited to a group consisting of a horizontal computed tomography scan of the third vertebra or a horizontal computed tomography scan of fourth vertebra. In another preferred embodiment, the muscle is a portion of the lumbar paraspinal muscles, which is selected from but not limited to the following: transverse abdominis, rectus abdominis, internal oblique, external oblique, psoas, quadratus lumborum, paraspinal muscle and combinations thereof. In one more preferred embodiment, to identify the amount or the distribution density of muscle, a muscle distribution map is generated under the condition that the HU value of the computed tomography scan is ranged from −29 HU to 150 HU in the second selection step. In still one more embodiment, the preset window is limited between 300 HU to 500 HU, the preset window level is not limited between 40 HU to 50 HU and the preset HU value is not limited between −29 HU to 150 HU.

Figure 2:
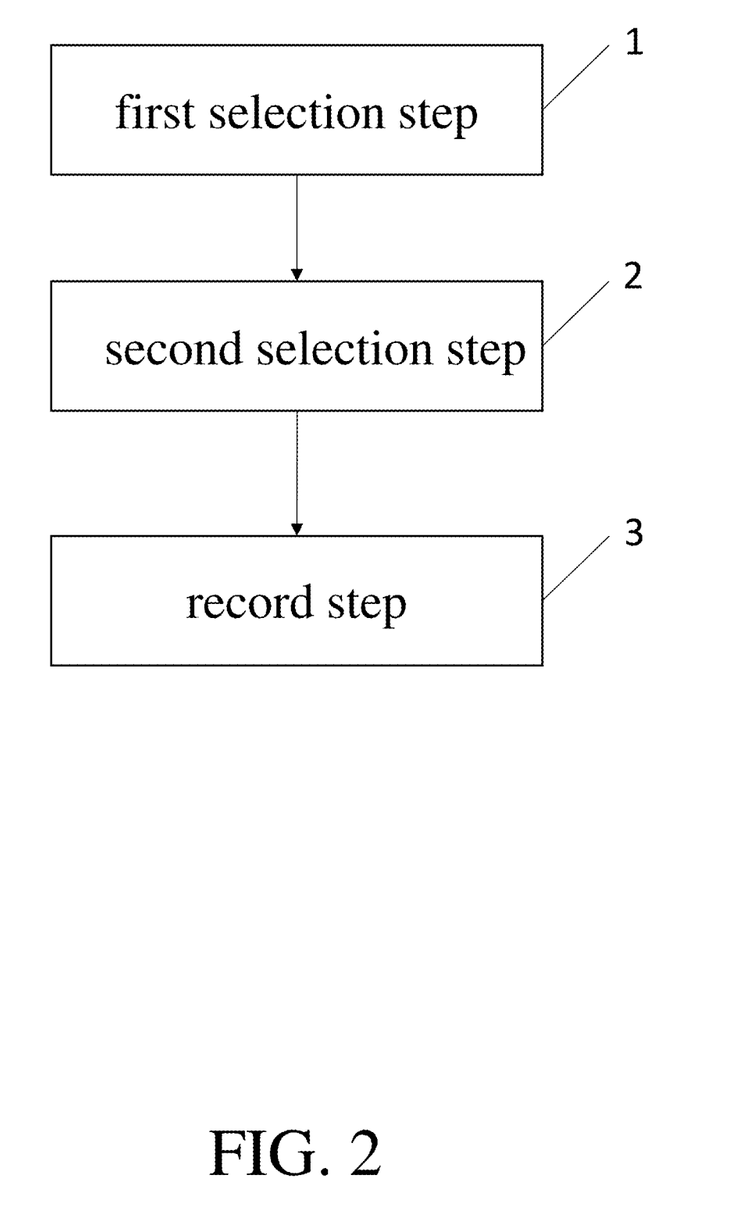
Figure 3:
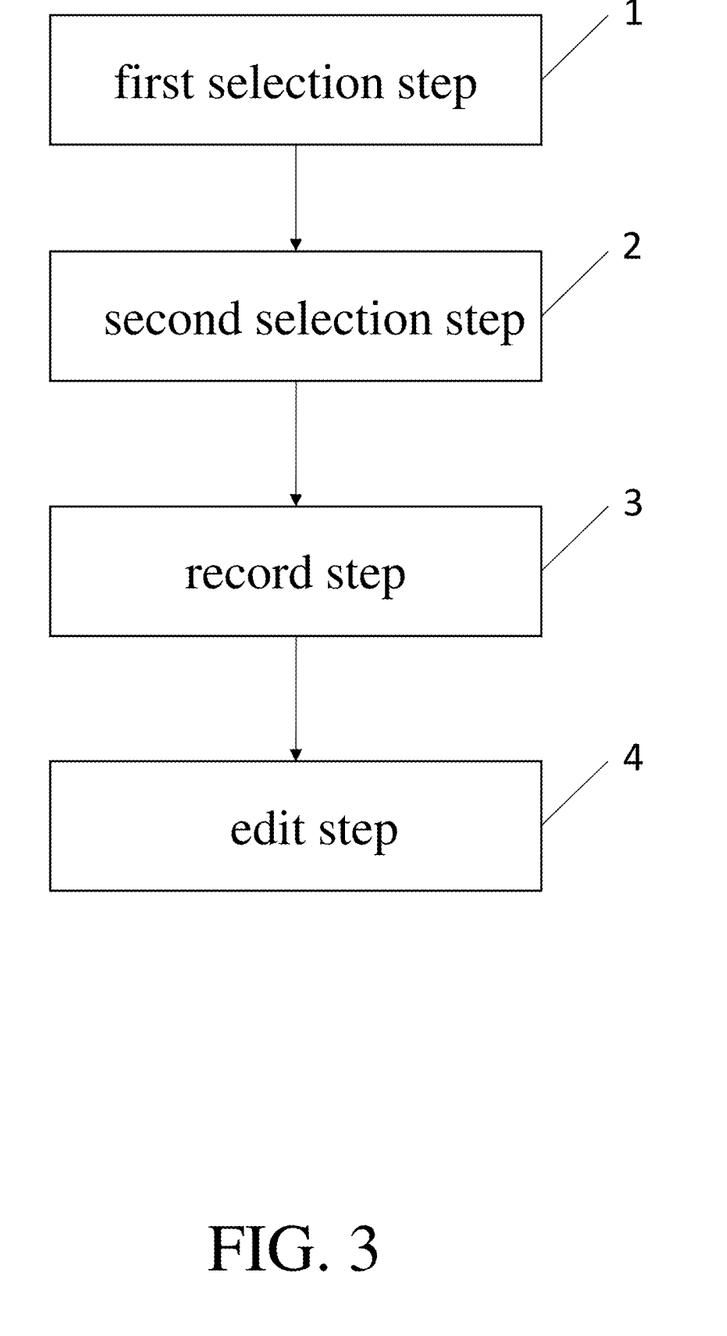

More preferably, as shown in FIG. 2, to record or access the frame selection information and the muscle information, a record step (3) is further included so as to store the frame selection information in a record module after the first selection step (1) and to store the muscle distribution map and the muscle information in the record module after the second selection step (2). In one preferred embodiment, as shown in FIG. 3, an edit step is further included to sort the muscle distribution maps in sequence according to the date and time when the second selection step (2) is performed, to edit those muscle distribution maps sorted in sequence into a video such that the observer may better understand the variations in the muscles, or to integrate the muscle distribution maps into a three-dimensional stereoscopic map.

More preferably, to enhance the velocity and the quality of measuring muscle mass or to provide a benchmark for assisting judgement, an analysis module is used to automatically frame out the fascia area in the computed tomography scan in the first selection step (1). In detail, the analysis module may receive a frame selection reference object and then organize and summarize a detail features within the frame selection range of the frame selection reference object. Also, by using the detail features, a portion of the computed tomography scan image matching the detail features is framed out to obtain frame selection information. In one preferred embodiment, the detail features include but not limited to the following: orientation, shading, texture, bump or relative position. Understandably, the frame selection of the traditional computer scanning is manually framed out, and then the experience abundance and the observation of the framer is severely challenged. Besides, due to the finite indentation ability of the human eyes, errors usually is unavoidable in the manually frame selection and then the final measured result of the computed tomography scan usually is not precise. In contrary, the invention presents an "intelligent learning" approach to determine the computed tomography scan image, also may adjust the classification of the frame selection reference object according to the symptom to the measure so as to be suitable for different application situations. In particularly, one object of this invention is measure and determine the symptoms of the sarcopenia. Hence, it has to initially acquire a horizontal computed tomography scan of the third vertebra or a horizontal computed tomography scan of fourth vertebra, and then to frame out some muscles related to the sarcopenia in the above computed tomography scan so as to determine whether the tester having the sarcopenia symptom according to the muscle mass in the framed range. At this time, to automatically frame out any muscle related to the sarcopenia by the analysis module when the computed tomography scan image is provided, the used frame selection reference object is at least a computed tomography scan image which has been framed out any muscle related to the sarcopenia such that the analysis module may use it as the benchmark for framing out. Understandably, the object of framing out the muscle(s) related to the sarcopenia is to effectively analysis or determine the symptoms of the sarcopenia. Particularly, the object of the invention is to measure the muscle mass. Hence, it may be adjusted according to the computed tomography scan images of muscles, tissues or bones in different portions of the human body, such that the detail information of the to be measured portion of the human body may be achieved. Hence, the framed out portion is not limited only to the muscles associated with the sarcopenia.

Figure 4:
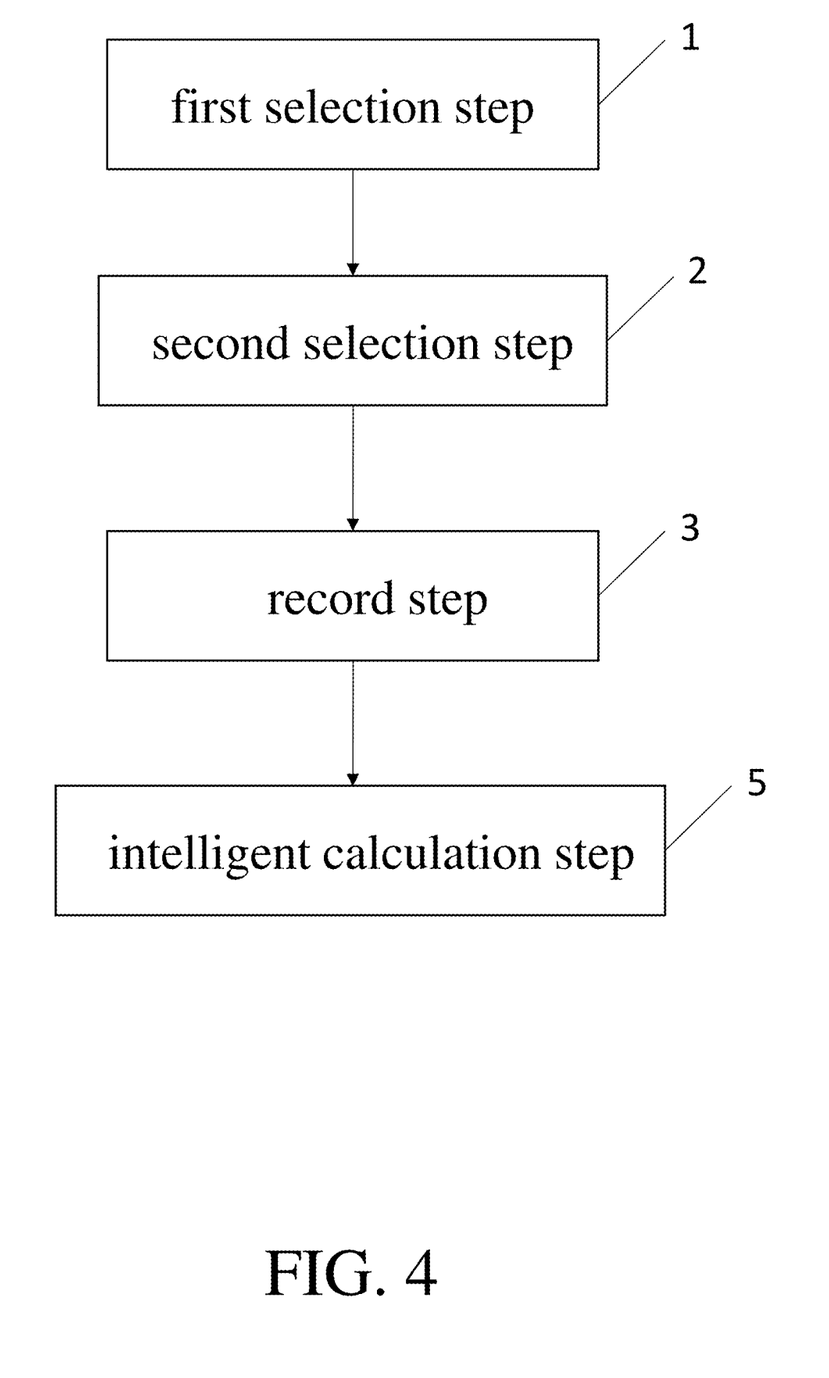

More preferably, as shown in FIG. 4, to make the muscle mass of the muscle easier to be interpreted or be used as a benchmark for the subsequent research, an intelligent operation step (5) is further included after the record step (3). In this step, an operation module is used to present the muscle information in the digital format for expressing mass, density or distribution of the muscle. In this step, the operation module is connected with the record module via signal so as to receive the muscle information.

Figure 5A:
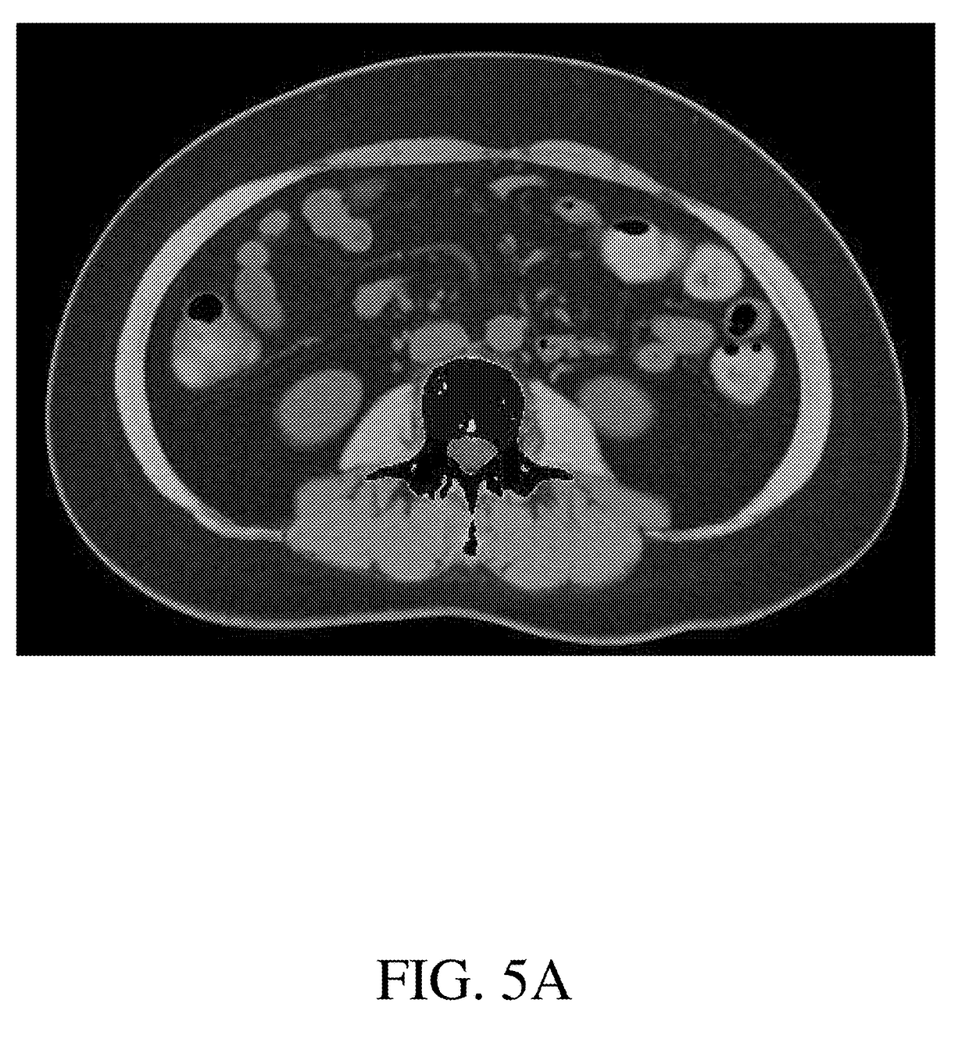
FIG. 5A to FIG. 5E are a series of schematic of the computed tomography scan which are used to discloses the procedure of the invention for framing out the muscles.
Figure 5B:
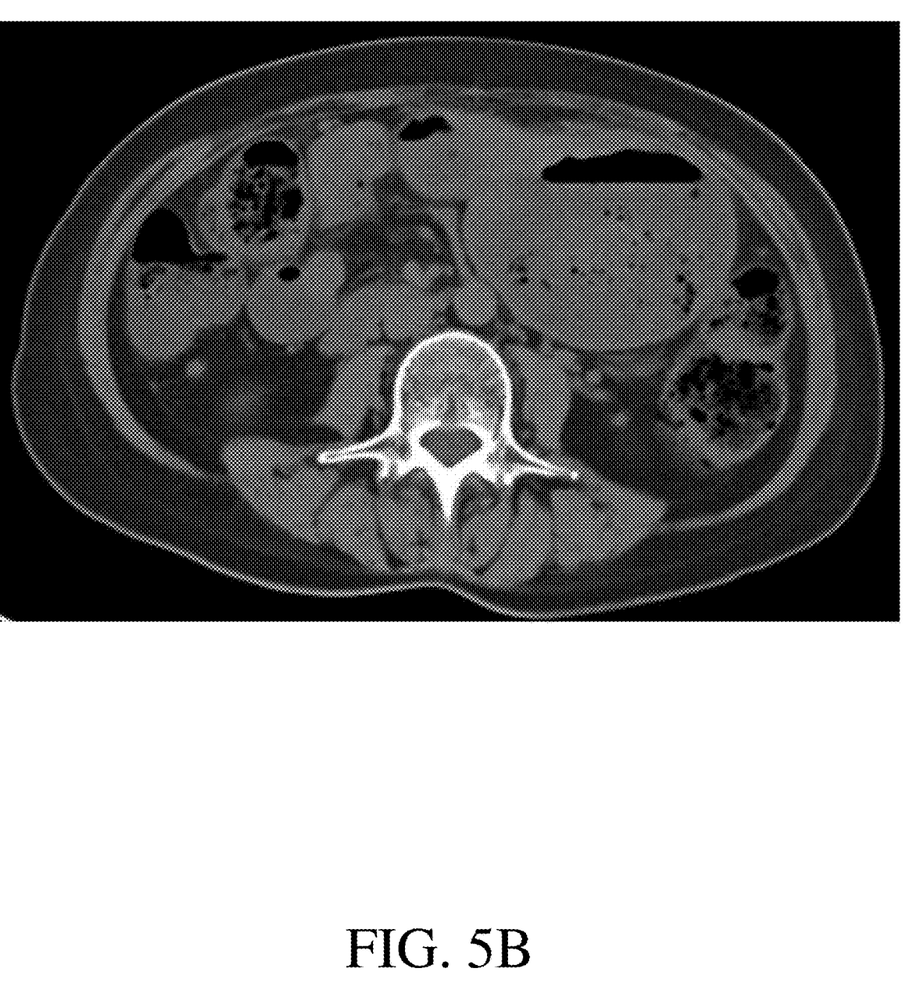
Figure 5C:
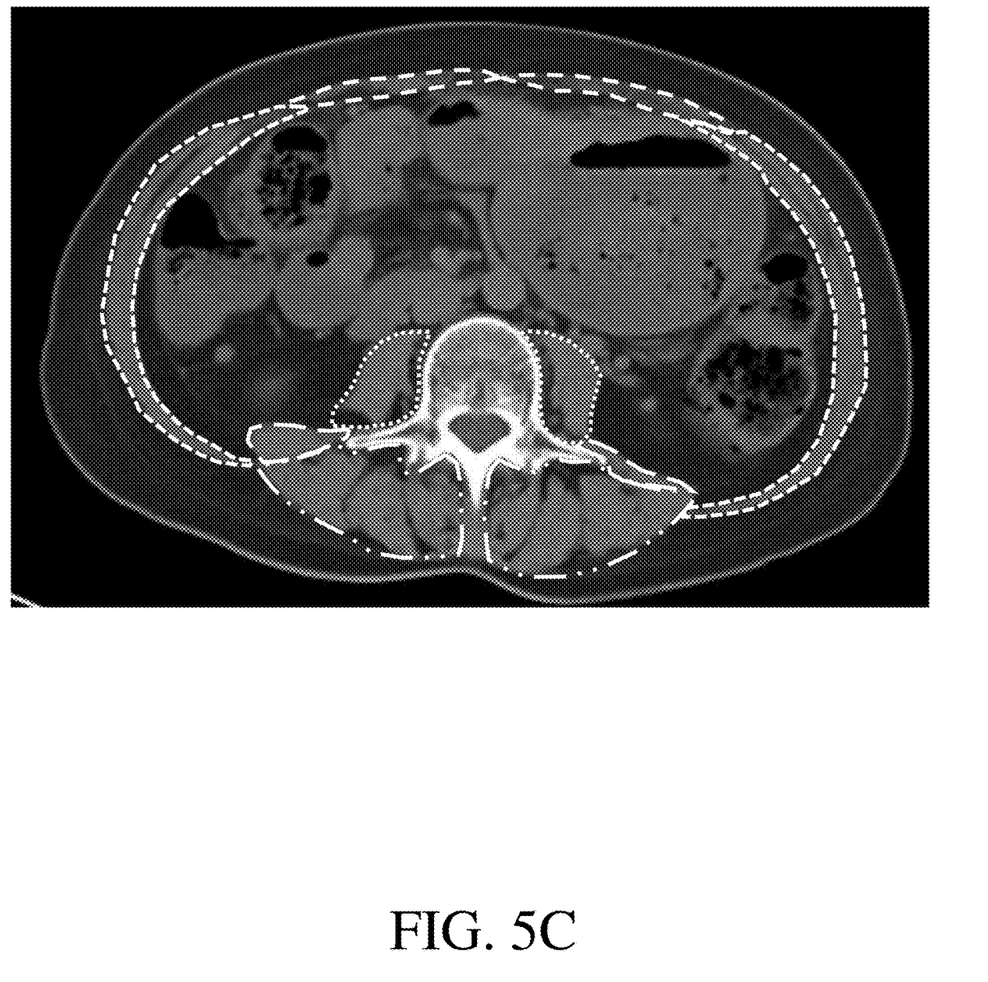

More preferably, FIG. 5B, FIG. 5C and FIG. 5 are a series of schematic of the computed tomography scan. Moreover, FIG. 5B is result of the general computed tomography scan image, FIG. 5C is the automatically framed out result along fascia in the computed tomography scan image according to this invention, and FIG. 5E is used to present the schematic of the muscle distribution map after the HU value is adjusted in the second selection step (2). In one preferred embodiment, FIG. 5C is a computed tomography scan acquired with the situation that the window width is 450 HU and the window level is 45 HU. In another preferred embodiment, as shown in FIG. 5C, different ranges framed out by different dotted lines are selected respectively by the analysis module in reference with the information of the frame selection reference object and is selected according to the detail features of the frame selection reference object. Understandly, the automatic selection mechanism may avoid the experience required by the manually selection mechanism, and then reduce error, reduce manpower and improve effectiveness of muscle measurement. Still in a preferred embodiment, as shown in FIG. 5E, in the second selection step, the contrast between muscle portions and non-muscle portions in the muscle distribution map is increased because the HU value is the computed tomography scan has been adjusted, and then the muscle information in the muscle distribution map is easily determined by the human body or by the machine.

The following is used to describe the second embodiment of the present invention.

As shown in FIG. 1, the present invention provides another method for measuring muscle mass which comprises two selection steps. In the first selection step, a first frame selection information and a second frame selection information are obtained by using a frame to select a first fascia region and a second fascia region from a provided computed tomography image under the condition that the window width ranges from 300 HU to 500 HU and the window level ranges from 40 HU to 50 HU, wherein the first selected range of the fascia region includes a first muscle and the second selected range of the fascia region includes a second muscle. In the second selection step, a first muscle information of the first muscle is obtained by calculating a pixel value in the frame-selected first fascia region and a second muscle information of the first muscle is obtained by calculating a pixel value in the frame-selected second fascia region under the condition that the HU value of the CT image ranges from −29 HU to 150 HU. In one preferred embodiment, to measure the muscle mass of the lumbar paraspinal muscles for determining the symptoms or the severity of the sarcopenia, the computed tomography image is optionally selected from but not limited to a group consisting of a horizontal computed tomography scan of the third vertebra or a horizontal computed tomography scan of fourth vertebra. In another preferred embodiment, the first muscle is a portion of the lumbar paraspinal muscles, which include but not limited to the following: transverse abdominis, rectus abdominis, internal oblique, external oblique, psoas, quadratus lumborum, paraspinal muscle and combinations thereof. Also, the second muscle is a portion of the lumbar paraspinal muscles, which include but not limited to the following: transverse abdominis, rectus abdominis, internal oblique, external oblique, psoas, quadratus lumborum, paraspinal muscle and combinations thereof. In one more preferred embodiment, to identify the amount or the distribution density of the first muscle and the second muscle, a muscle distribution map is generated under the condition that the HU value of the computed tomography scan is ranged from −29 HU to 150 HU in the second selection step.

In still one more preferred embodiment, as shown in FIG. 2, to record or access the frame selection information and the muscle information, a record step (3) is further included so as to store the first frame selection information and the second frame selection information in a record module after the first selection step (1) and to store the first muscle information and the second muscle information in the record module after the second selection step (2). In still one more preferred embodiment, as shown in FIG. 3, an edit step is further included to sort the muscle distribution maps in sequence according to the date and time when the second selection step (2) is performed, to edit those muscle distribution maps sorted in sequence into a video such that the observer may better understand the variations in the muscles, or to integrate the muscle distribution maps into a three-dimensional stereoscopic map.

More preferably, an analysis module is used to automatically frame out the first fascia area and the second fascia area in the computed tomography scan in the first selection step (1). In detail, the analysis module may receive a frame selection reference object and then organize and summarize a detail features within the frame selection range of the frame selection reference object. Also, by using the detail features, a portion of the computed tomography scan image matching the detail features is framed out to obtain a first frame selection information and a second frame selection information. Anyway, the automatic frame machoism is essentially similar with that of the first preferred embodiment of this invention. Hence, the details are not repeated described herein.

More preferably, as shown in FIG. 4, an intelligent operation step (5) is further included after the record step (3). In this step, an operation module is used to present the first muscle information and then second muscle information in the digital format for expressing mass, density or distribution of the first muscle and the second muscle respectively. In this step, the operation module is connected with the record module via signal so as to receive the first muscle information and the second muscle information.

Figure 5D:
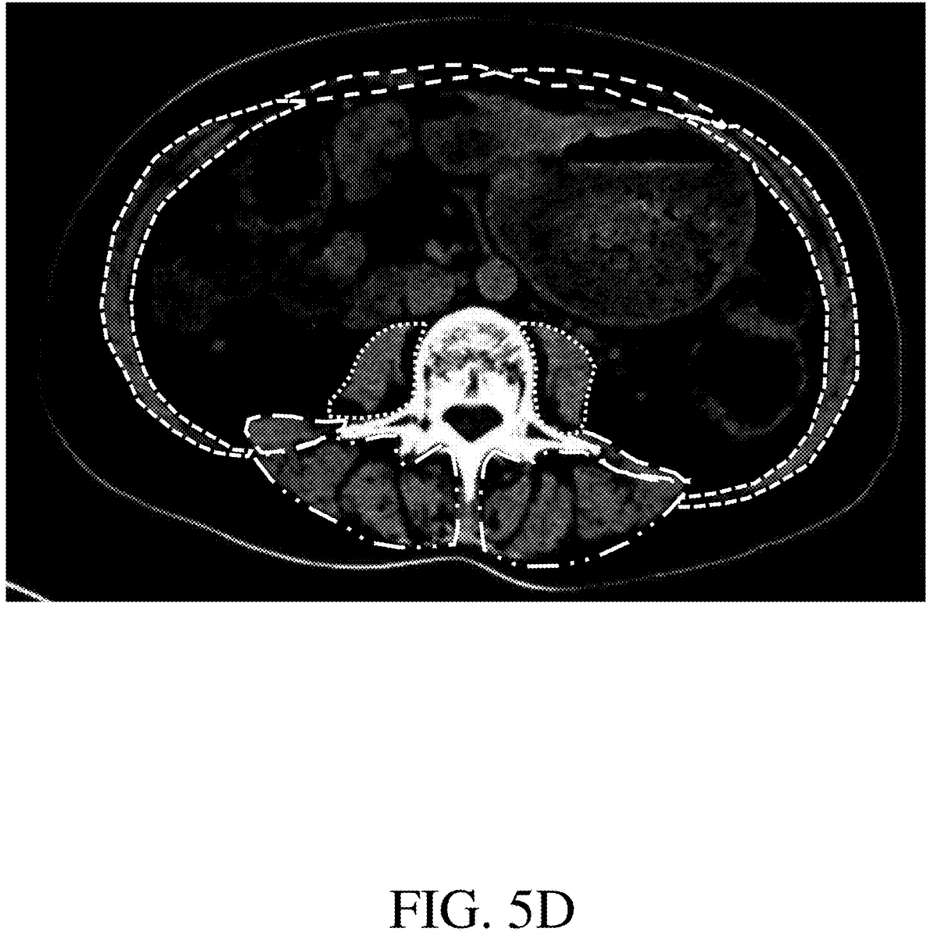
Figure 5E:
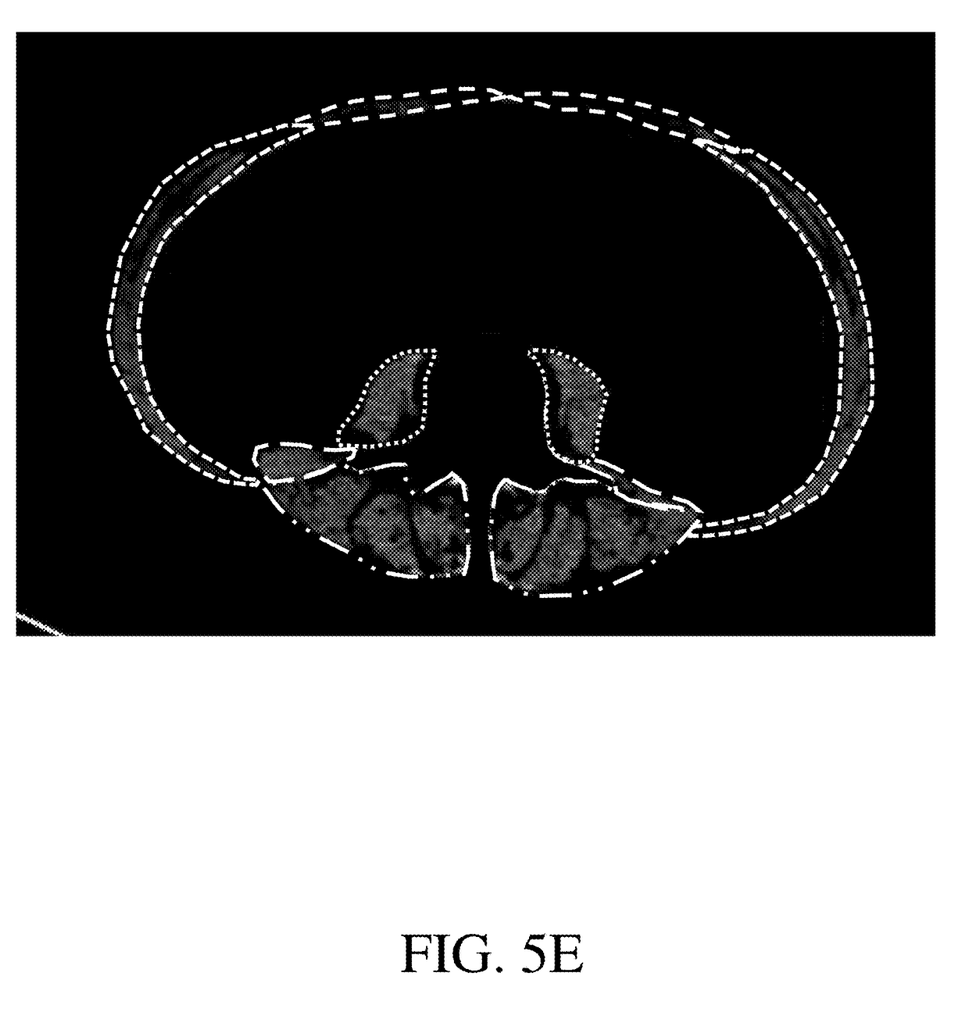

More preferably, FIG. 5A is the framed out result after using AI (artificial intelligence) to automatically classify the muscles in the computed tomography scan image result. In details, by using AI to automatically frame out, any fascia on the muscle surface of any muscle on the computed tomography scan image may be framed out individually such that the first frame selection information and the second selection information may be obtained. After that, muscle mass of any specific muscle may be analyzed. Moreover, FIG. 5B is result of the general computed tomography scan image, and FIG. 5C is frame selection result by using the computed tomography scan image shown in FIG. 5B to frame out the fascia on the muscle surface of each muscle with the situation that the window width is 440 HU and the window level is 45 HU. In particular, five dotted lines are used to frame out the fascia on five muscles respectively in the FIG. 5C, the result acquired in the second selection step (2) after the HU value is adjusted is shown in FIG. 5D, wherein the HU value is adjusted to between −29 HU to 150 HU such that the muscle portions covered by the fascia are appeared and is benefit for the following operation about mass or data of the muscle, and FIG. 5E presents the quantitative results of the mass region on the framed out range in the FIG. 5D. In one preferred embodiment, as shown in FIG. 5C to FIG. 5E, the range framed out by each dotted line is selected by using the analysis module to refer the information of the frame selection reference object and then decided by the detail feature of the frame selection reference object. Understandably, the automatic selection mechanism may avoid the experience required by the manually selection mechanism, and then reduce error, reduce manpower and improve effectiveness of muscle measurement. Still in a preferred embodiment, as shown in FIG. 5D, in the second selection step, the contrast between muscle portions and non-muscle portions in the muscle distribution map is increased because the HU value is the computed tomography scan has been adjusted, and then the muscle information in the muscle distribution map is easily determined by the human body or by the machine. Also in another preferred embodiment, more and more frame selection reference information is included. Understandably, the amount of the frame selection reference information corresponds to the amount of the muscle and is sorted by number, although it is not limited herein.

More preferably, in the second selection step (2), muscles, tissues or bones of human body may be measured according to the preset HU value. In particular, as shown in Table 1, muscle distribution, muscle density or muscle mass of the skeletal muscle may be appeared on the computed tomography scan image under the situation that HU value is preset in a range from −29 HU to 150 HU. Understandably, the HU value may be properly preset according to the human body portions to be measured, but not is limited to measure the skeletal muscle.

TABLE 1

| Tissues | HU value range |
| --- | --- |
| Skeletal muscle | −29~150 |
| intermuscular adipose tissue | −190~−30 |
| Visceral adipose tissue | −150~−50 |
| Subcutaneous adipose tissue | −190~−30 |
| Bone | 250~2000 |

More preferably, the general methods for measuring human body include but not limited to the following: bioelectrical impedance analysis (BIA), computed tomography (CT), magnetic resonance imaging (MRI), dual-energy X-ray absorptiometry (DXA), ultrasonic echo method or naked eye observation. Among all of these, CT uses the digital geometrical process to reconstruct a three-dimensional radiological medical image, and is a medical diagnosis tool combining X-ray technology and computer operation. Wherein, due to different materials having different absorption capacities or different radiodensities, this technology mainly irradiate light along a single axis to an object in rotation and then uses the computer three-dimensional technology to reconstruct the tomographic image. In one preferred embodiment, a MRI contrast agent is used to enhance the contrast between different tissues before a computed tomography scan is performed. Wherein, the MRI contrast agent is a material may be injected into the human body through the vein and then absorbed by the human body tissues along with the distribution of the blood vessels. The MRI contrast agent may modify the contrast and brightness of different tissues when shooting images, such that blood vessels, tumors, organs, muscles or other portions of the human body may be more clear and easy to read. In another preferred embodiment, the window width indicates the CT value range included in the computed tomography image and the window level indicates the average of the upper limitation and the lower limitation of the window width. By processing the window width and the window level, the scan image of the corresponding human body tissues may be acquired. In one more preferred embodiment, the three-dimensional image of all tissues, organs, bones, or muscles of the human body may be clearly displayed by stacking the CI images layer by layer, Hence, it may be used by the medical staff as an important reference for diagnosing or treating the physical symptoms. Because the computed tomography scan is a non-invasive technology may quickly and simply reconstruct the three-dimensional image inside human body, it may display situations of most portions of the human body and significantly increase the accuracy of disease diagnosis. Therefore, the invention uses the computed tomography scan to measure the muscle mass.

More preferably, to measure different muscle diseases or symptoms, each of the muscle, the first muscle or the second muscle is a portion of human muscle groups. The human muscle groups include but not limited to the following: lumbar paraspinal muscles, leg muscles, chest muscles, back muscles, abdominal muscles, biceps muscles, triceps muscles or core muscles. In one preferred embodiment, the lumbar paraspinal muscles include but not limited to the following: intertransverse process muscles, quadratus lumborum muscles, multifidus muscles, lumbar iliocostalis muscles, longissimus muscles and psoas major muscles. In another preferred embodiment, the leg muscles include but not limited to the following: thigh muscles and calf muscles. The thigh muscles include but not limited to the following: sartorius muscles, quadriceps muscle, tensor fasciae late muscles. The back thigh muscles include but not limited to the following: biceps femoris muscles, semitendinosus muscles, and semimembranosus muscles. The inner thigh muscles include but not limited to the following: pectineus muscles, adductor longus muscles, adductor brevis muscles, adductor magnus muscles, and gracilis muscles. The calf muscles include but not limited to the following: front calf muscles, outer calf muscles and back calf muscles. The front calf muscles include but not limited to the following: tibialis anterior muscles, extensor longus digitorum muscles, and extensor longus pollicis muscles. The outer calf muscles include but not limited to following: peroneus longus muscles, and peroneus brevis muscles. The back calf muscles include but not limited to the following: triceps surae muscles, flexor digitorum longus muscles, flexor pollicis longus muscles, and tibialis posterior muscles. In one more preferred embodiment, the chest muscles include but not limited to the following: pectoralis major muscles, pectoralis minor muscles, serratus anterior muscles, and intercostal muscles. In still one more preferred embodiment, the back muscles include but not limited to the following: trapezius muscles, latissimus dorsi muscles, teres major muscles, teres minor muscles, erector spinae muscles, and rhomboids muscles. In still one more preferred embodiment, the abdominal muscles include but not limited to the following: rectus abdominis muscles, internal oblique muscles, transverse abdominis muscles and external oblique muscles. In still one more preferred embodiment, the shoulder muscles include but not limited to the following: anterior deltoid muscles, middle deltoid muscles, and rear deltoid muscles. In still one more preferred embodiment, the core muscles indicate the muscles from below the diaphragm to the pelvic floor and surrounding the waist, abdomen and central trunk. The core muscles include but not limited to the following: transverse abdominis muscles, lumber multifidi muscles, internal oblique muscles, external oblique muscles, rectus abdominis muscles, quadratus lumborum muscles, erector spinae muscles, respiratory diaphragm muscles and pelvic floor muscles. Particularly, in a further preferred embodiment, the muscle, the first muscle or the second muscle may include one or more muscles listed above although is not limited herein.

More preferably, the muscle diseases include but not limited to the following: sarcopenia, muscle atrophy and muscle inflammation. Moreover, the sarcopenia is a symptom that weight and function of the skeletal muscle are continuously lost and weaken throughout the human body. With the reduction of muscle mass of skeletal muscle, slow walking, decreased grip strength, labored movement, repeated falls and body weight loss are unavoidable. Hence, the life qualify is greatly degraded, even disability is happened. The sarcopenia usually occurs with advanced age and chronic diseases. Hence, it is more than worth the loss if it is not found early and appropriately treated in the early stage of disability. Mild symptoms may easily weaken limbs health and increase falling probability. Severe symptoms may lead to disability and prolonged lying in bed. Also, muscle atrophy indices the gradual loss of muscle mass and/or gradual weakening and degeneration of muscles. The present invention not only may measure the symptoms of sarcopenia, but also may perform computed tomography scans on the muscles of specific portions of human body. Therefore, the present invention may observe whether there are other muscle diseases so as to prevent or control muscle diseases, or may promote muscle re-growth so that the muscle mass has been reduced due to a certain reason is restored to the original level, or may restore the muscle strength has been reduced due to a certain reason back to the original level.

More preferably, to effectively measure the muscle mass so as to treat or prevent symptoms such as sarcopenia or muscle steatosis immediately, the computed tomography scan may be used to measure total abdominal muscle area (TAMA), intermuscular adipose tissue area (IMAT) or skeletal muscle area (SMA). Moreover, the total mass area measured by computed tomography scan measurement includes normal attenuation muscle area (NAMA) and low attenuation muscle area (LAMA). Particularly, NAMA is less prone to fat infiltration and is a high-quality muscle area, but LANA is prone to have fat cells more likely found in muscle fibers and is a poor-quality muscle area. Usually, LAMA is used as an indicator of physical defects or poor metabolism. Besides, the density of LAMA is lower in the CT scan image due to higher fat content in LANA. Also, because the L3 lumbar vertebra is highly related to the muscle mass of the whole human body, its CT scan image is suitable to be used a basis for diagnosing muscle mass. In one preferred embodiment, CT scan may be performed by using Somatom Definition (Siemens Healthineers, Erlangen, Germany), Discovery CT750 HD (GE Healthcare, Milwaukee, WI, USA) or LightSpeed VCT scanner (GE Healthcare). The preset parameters for CT scan include but not limited to the following: 120 kVp, automatic medicine preparation (CareDose 4D, Siemen Healthineers, automA and smartmA, GE Healthcare), matrix of 512×512, collimation of 0.625 mm or any combination thereof. In another preferred embodiment, image and data acquired by CT scan may be reconstructed by using the "soft tissue filtered back projection technology" (B30f Kernel, Siemens Healthineers, Standard Kernel, GE Healthcare) to setup a slice thickness, such as but not limited to 5 mm. In still another preferred embodiment, optionally but not limited, 100e150 Ml iopromide (Ultravist 370 or Ultravist 300, Bayer Schering Pharma, Berlin, Germany) may be used to enhance the contrast, a power injector with 2.5e3 mL/sec injection rate when an automatic intravenous injector is used, or scan is fixed delay 70 second after the contrast injection is fully injected. Understandably, the CT scan may be used to measure any portion of the spine but not be limited to the L3 lumbar vertebrae. In one more preferred embodiment, CT image is performed by using "Analytic Morphomics" which is a semi-automatic computational image processing system written in Mathlab, wherein acquired CT image is coded in the DICOM format and stored in a space database. In still one more preferred embodiment, CT images may be segmented by using the medical image analysis software. Particularly, by using the CT image of third vertebra as example, it may automatically identify and separate muscle area, bone area, SAT (subcutaneous adipose tissue) area and VAT (visceral adipose tissue) area. In one further preferred embodiment, the used medical image analysis software is sliceOmatic, although it is not limited to this.

More preferably, the axial CT slices of the L3 lumbar vertebra may be automatically selected by using a convolutional network (FCN) segmentation technology so as to automatically generate the following CT image segments: total order abdominal muscle area (TAMA), visceral fat area and subcutaneous fat area. Particularly, TAMA includes all muscles on the selected image, such as psoas major muscles, paraspinal muscles, transversus abdominis muscles, rectus abdominis muscles, quadratus lumborum muscles, internal obliques muscles and external obliques muscles. During the period of measuring muscle mass, TAMA may be divided into three portions: IMAT for showing adipose tissue between muscles and muscle fibers (shown when the HU value of the CT image is from −190 HU to −30 HU), NAMA for showing healthy muscles (shown when the HU value of the CT image is from 30 HU to 150 HU), and LAMA for showing the un-heathy muscles (shown when the HU value of the CT image is from −29 HU to 29 Hu). In one preferred embodiment, SAS software (SAS institute, Inc., Cary, NC, USA) or R software (R Foundation for Statistical Computing, Vienna, Austria) may be used to analyze the muscle mass. In another preferred embodiment, Pearson correlation coefficient is used to evaluate SMA, TAMA degradation and NAMA/TAMA index. To specifically evaluate whether the muscle mass is normal or not, the numerical size of a specificity T value may be used as reference, wherein T value is the ratio between difference between measurement value and young adult's mean value and younger's standard deviation. If measured T value is larger than −1, LAMA value is less than 1 o IMAT value is less 1, the muscle may be viewed as normal without potential danger. If measured T value is not larger than −1.0 and not less than −2.0, measured T value is less than −2, measured T value is not larger than 2 but is larger than 1, LAMA value is larger than 2 or IMAT value is larger than 2, the condition of the muscle is abnormal. At this time, muscle steatosis or sarcopenia may happen, and further health examination is required.

More preferably, Pearson correlation coefficient or Tukey's may be used to evaluate the association difference between lumbar vertebra levels. In some previous studies, it had been proven that CT measurements of SMA is correlated with whole-body muscle mass of healthy adults and that mean skeletal muscle radiation attenuation (SMRA) is correlated with muscle fat content and body function. Wherein, SMRA is calculated as the average HU value of all pixels included in SMA and skeletal muscle index (SMI) is the ration between SMA and the square of height. In one preferred embodiment, when CT image is performed with L3 lumbar vertebrae, the critical values of SMA, SMI and SMRA is 99.2 cm$^2$, 34.4 cm$^2$/m$^2$ and 34.3 Hu in sequence for female sarcopenia patients and is 144.3 cm$^2$, 45.4 cm$^2$/m$^2$ and 38.5 Hu in sequence for male sarcopenia patients. Therefore, these critical values listed above may be used as reference for determining whether sarcopenia is existed or not.

To compare with the prior arts, the effect of the present invention is that the sarcopenia is not determined by using physical fitness but uses computed tomography technology to obtain accurate muscle mass date. Hence, precise determine results may be achieved, and muscle may be traced during the following treating stage or recovering stage for recording the results of increasing muscle mass. Besides, when using computed tomography technology to measure muscle mass, the present invention automatically frames out a fascia area to be measured and is significantly different than the prior arts that the medical staff manually frame out. Hence, the present invention may ensure the fascia portions on the surfaces of all muscles are all framed out without omission during each frame selection. Further, by adjusting HU value, the muscles portions on the computed tomography scan image are significantly highlighted so that precise muscle mass data may be acquired.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method for measuring muscle mass, comprising:
a first selection step, wherein a frame selection information is obtained by using a frame to select a fascia region from a provided computed tomography image under the condition that the window width ranges from 300 HU to 500 HU and the window level ranges from 40 HU to 50 HU, wherein the selected range of the fascia region includes a muscle; and
a second selection step, wherein a muscle information of the muscle is obtained by calculating a pixel value in the frame-selected fascia region under the condition that the HU value of the CT image ranges from −29 HU to 150 HU.

2. The method as claimed in claim 1, wherein the computed tomography image is selected from a group consisting of a horizontal computed tomography scan of the third vertebra or a horizontal computed tomography scan of fourth vertebra, and wherein the muscle is chosen from a group consisting of the following: transverse abdominis, rectus abdominis, internal oblique, external oblique, psoas, quadratus lumborum, paraspinal muscle and combinations thereof.

3. The method as claimed in claim 1, further comprising a record step to store the frame selection information in a record module after the first selection step and to store the muscle information in the record module after the second selection step.

4. The method as claimed in claim 3, further comprising using an analysis module to automatically select the fascia region from the computed tomography image in the first selection step, wherein the analysis module receives a frame selection reference object and then organize and summarize a detail feature within the frame selection range of the frame selection reference object, wherein the analysis module use the detail feature to obtain the frame selection information by framing out a portion of the computed tomography image which having the same detail feature.

5. The method as claimed in claim 4, further comprising an intelligent calculation step after the record step, wherein a calculation module is used to present the muscle information in the digital format so as to express one of the following of the muscle: mass, density and distribution, wherein the calculation module communicates with the record module to receive the muscle information through signal.

6. A method for measuring muscle mass, comprising:
a first selection step, wherein a first frame selection information and a second frame selection information are obtained by using a frame to select a first fascia region and a second fascia region from a provided computed tomography image under the condition that the window width ranges from 300 HU to 500 HU and the window level ranges from 40 HU to 50 HU, wherein the first selected range of the fascia region includes a first muscle and the second selected range of the fascia region includes a second muscle; and
a second selection step, wherein a first muscle information of the first muscle is obtained by calculating a pixel value in the frame-selected first fascia region and a second muscle information of the first muscle is obtained by calculating a pixel value in the frame-selected second fascia region under the condition that the HU value of the CT image ranges from −29 HU to 150 HU.

7. The method as claimed in claim 6, wherein the computed tomography image is selected from a group consisting of a horizontal computed tomography scan of the third vertebra or a horizontal computed tomography scan of fourth vertebra, wherein the first muscle is chosen from a group consisting of the following: transverse abdominis, rectus abdominis, internal oblique, external oblique, psoas, quadratus lumborum, paraspinal muscle and combinations thereof, and wherein the second muscle is chosen from a group consisting of the following: transverse abdominis, rectus abdominis, internal oblique, external oblique, psoas, quadratus lumborum, paraspinal muscle and combinations thereof.

8. The method as claimed in claim 6, further comprising a record step to store the frame selection information in a record module after the first selection step and to store the first muscle information and the second muscle information in the record module after the second selection step.

9. The method as claimed in claim 8, further comprising using an analysis module to automatically select the first fascia region and the second fascia region from the computed tomography image in the first selection step, wherein the analysis module receives a frame selection reference object and then organize and summarize a detail feature within the frame selection range of the frame selection reference object, wherein the analysis module use the detail feature to obtain the first frame selection information and the second frame selection information by framing out a portion of the computed tomography image which having the same detail feature.

10. The method as claimed in claim 9, further comprising an intelligent calculation step after the record step, wherein a calculation module is used to present the first muscle information and the second muscle information in the digital format so as to express one of the following the first muscle and the second muscle: mass, density and distribution, wherein the calculation module communicates with the record module to receive the first muscle information and the second muscle information through signal.

\* \* \* \* \*